United States Patent
Tran et al.

(10) Patent No.: US 9,494,486 B2
(45) Date of Patent: Nov. 15, 2016

(54) METHOD OF INSPECTING IMPACTS OBSERVED IN FAN CASINGS

(75) Inventors: Julien Tran, Pontoise (FR); Richard Lavignotte, Alforville (FR)

(73) Assignee: SNECMA, Paris (FR)

( * ) Notice: Subject to any disclaimer, the term of this patent is extended or adjusted under 35 U.S.C. 154(b) by 275 days.

(21) Appl. No.: 14/007,269

(22) PCT Filed: Mar. 15, 2012

(86) PCT No.: PCT/FR2012/050542
§ 371 (c)(1),
(2), (4) Date: Sep. 24, 2013

(87) PCT Pub. No.: WO2012/131211
PCT Pub. Date: Oct. 4, 2012

(65) Prior Publication Data
US 2014/0020485 A1    Jan. 23, 2014

(30) Foreign Application Priority Data
Mar. 25, 2011  (FR) ...................................... 11 52492

(51) Int. Cl.
*G01M 13/00*  (2006.01)
*F01D 21/00*  (2006.01)
(Continued)

(52) U.S. Cl.
CPC ................. *G01M 13/00* (2013.01); *B64C 5/06* (2013.01); *F01D 21/003* (2013.01);
(Continued)

(58) Field of Classification Search
CPC ................... G01N 21/8803; G01N 2021/8854; G01N 2021/8858; G01N 2021/8874
See application file for complete search history.

(56) References Cited

U.S. PATENT DOCUMENTS 4,950,911 A * 8/1990 Williams et al. ........ 250/559.45
5,293,309 A * 3/1994 Sakai et al. ..................... 705/29
(Continued)

FOREIGN PATENT DOCUMENTS

JP    2005-339249    12/2005

OTHER PUBLICATIONS

International Search Report as issued for PCT/FR2012/050542.

*Primary Examiner* — Lisa Caputo
*Assistant Examiner* — Tran M Tran
(74) *Attorney, Agent, or Firm* — Pillsbury Winthrop Shaw Pittman LLP

(57) ABSTRACT

A method for inspecting impacts present on an internal face of a fan casing, the method including: spotting a first impact present on the internal face of the fan casing; delimiting an inspection area containing the first impact; spotting the various impacts present in the delimited inspection area, the various spotted impacts forming a set of impacts to be considered; measuring, for each impact that is to be considered, the depth of length of the impact; for each impact to be considered, determining a harmfulness value, using at least one chart relating the depth and length of each impact to be considered to a level of harmfulness; determining, for the inspection area containing the first impact, a total harmfulness value by adding together the harmfulness level determined for each impact to be considered.

11 Claims, 2 Drawing Sheets

(51) Int. Cl.
  *F01D 21/04* (2006.01)
  *G01N 21/88* (2006.01)
  *G01N 21/954* (2006.01)
  *B64C 5/06* (2006.01)
  *G01N 17/00* (2006.01)
  *G01B 3/00* (2006.01)
  *B64D 45/00* (2006.01)
  *B64C 3/14* (2006.01)

(52) U.S. Cl.
  CPC ......... *F01D 21/045* (2013.01); *G01N 21/8803* (2013.01); *G01N 21/954* (2013.01); *B64C 2003/146* (2013.01); *B64D 2045/0095* (2013.01); *F05B 2280/6003* (2013.01); *F05D 2260/80* (2013.01); *G01B 3/00* (2013.01); *G01N 17/00* (2013.01); *Y02T 50/672* (2013.01)

(56) References Cited

U.S. PATENT DOCUMENTS 6,219,930 B1 *   4/2001   Reid ............................... 33/562
6,779,159 B2 *   8/2004   Yokoyama et al. .......... 382/145
6,985,220 B1 *   1/2006   Chen et al. ................ 356/237.5
8,384,888 B2 *   2/2013   Yamane et al. ............ 356/237.2

* cited by examiner

METHOD OF INSPECTING IMPACTS OBSERVED IN FAN CASINGS

CROSS-REFERENCE TO RELATED APPLICATIONS

This is the U.S. National Stage of PCT/FR2012/050542, filed Mar. 15, 2012, which in turn claims priority to French Patent Application No. 1152492, filed Mar. 25, 2011, the entire contents of all applications are incorporated herein by reference in their entireties.

TECHNICAL FIELD OF THE INVENTION

The present invention relates to a method for inspecting impacts observed in fan casings of aircraft engines.

The field of the invention is generally that of aircraft engines, and more particularly that of monitoring the condition of these engines over the course of time. The present invention more precisely relates to fan casings; it is reminded that in such a context, a fan is generally a multiple shrouded propeller, which can be mounted in the front or even in the rear of jet engines, and the function of which is to promote an increase in the thrust generated by the jet engine, by accelerating the huge air mass passing therethrough before it is ejected into the atmosphere.

On some aircraft engines, fan casings, and in particular casings free of acoustic panels, are permanently subjected to impacts of foreign bodies having a very variable size; such bodies can for example be sand, hailstones, stones, birds . . . . Such impacts cause a local decrease in the casing thickness, which might alter the specific retention thereof.

These defects are most often noticed under the aircraft wing, during pre-flight inspections, or during regular inspections with engine removal in maintenance facilities.

TECHNOLOGICAL BACKGROUND OF THE INVENTION

Fan casings can be made of different materials, for example steel, composite. They are often made of aluminium. Repairing defects created by the abovementioned impacts has been contemplated by welding methods; but conventional welding processes, known as TIG, have been contemplated to refill these impacts but the conventional processes (TIG) do not yield satisfactory results, in particular on aluminium casings. Since such repairing is not applicable, this led, when impacts had high dimensions, to replace the full casing, or to dismount the engine.

One alternative to the full replacing of the casing is to obtain a technical validation which results in an administrative exemption, called CDR, to have the right to go on using impacted casings, possibly after slight alterations have been made on the observed defects. However, with the ageing of the fleet and the increasing number of engines in operation, these recurrent defects led to an increasing number of technical validation requests, and delays caused to restoration of parts subjected to the observed defects.

Consequently, in order to speed up the processing of this type of defects, acceptability criteria have been introduced in technical documentation. Therefore, there is now acceptance criteria of the defects discussed which allow a controller to quickly rule on the harmfulness of the defect without necessarily requiring an exemption. These acceptance criteria have been set based on statements on different casings and empirical laws allowing to rule on the specific retention of the casing as a function of its residual thickness.

These acceptance criteria have the form of trinomials of dimensions characterising the allowable defects; a first value of this trinomial is relative to a maximum allowable depth, a second value is relative to a maximum allowable length and a third value is relative to a minimum distance to be observed between two defects, in particular two defects related to an impact. Thus, for example, for an upstream zone of a casing, if a controller detects an impact having a depth 0.1524 mm (millimeters), he/she is aware that, by the existence of a trinomial associated with this depth, the defect considered should not have a length higher than 25.4 mm, and that no other defect should be present at a distance lower than 3.048 mm.

Unfortunately, these acceptance criteria only enable a restricted number defect to be accepted, because of the requirement to have available comparable reference values, and therefore do not prevent the number of requested validations from being increased; to overcome this problem, new acceptance criteria should constantly be introduced at each new noticed defect, which is not a viable solution in the long term. Furthermore, in view of the number of trinomials of values yet available, this inspection method may come out to be heavy and complex for controllers.

GENERAL DESCRIPTION OF THE INVENTION

The object of the invention offers a solution to the problems just set out by providing a simplified inspection method, making the task easier for controllers; the invention aims at simply evaluating the harmfulness of observed impacts in order to accelerate the processing of these defects. To do this, the present invention provides use of simple inspection tools, which require no particular training for use thereof, which substantially enable determining distances between different impacts to be avoided while allowing to quickly rule on whether these defects are accepted as to the specific retention of the fan casing.

The invention thus substantially relates to a method for inspecting impacts present on an internal face of a fan casing, said method being characterised in that it includes the different steps of:

spotting a first impact present in the internal face of the fan casing;

delimiting an inspection area including said first impact;

spotting the different impacts present on the delimited inspection area, said different spotted impacts forming a set of impacts to be considered;

measuring, for each impact to be considered, the depth and length of said impact;

for each impact to be considered, determining a level of harmfulness value, by means of at least one chart relating the depth and length of each impact to be considered to a level of harmfulness;

determining, for the inspection area including the first impact, a total level of harmfulness value by adding the level of harmfulness determined for each impact to be considered.

Besides the main characteristics just mentioned in the preceding paragraph, the method according to the invention can have one or more further characteristics form the following, considered singly or according to any technical possible combinations:

The step of delimiting an inspection area containing the first impact is performed by means of a mask.

The mask is rectangular in shape.

The dimensions of the mask depend on the location of the inspection area, a first mask having first dimensions being used for an upstream zone of the casing and/or a second mask having second dimensions being used for an abradable zone of the casing and/or a third mask having third dimensions being usable for a downstream zone of the casing.

The first mask is rectangular in shape, having a length 71 millimeters within ten percent, advantageously 71 millimeters, and a width 20 millimeters within ten percent, advantageously 20 millimeters, and/or the third mask is square in shape, having a side 250 millimeters within ten percent, advantageously 250 millimeters.

The mask is rectangular in shape, having the following characteristics:

a first side of the mask has a dimension between the fifth part of the chord of the casing vanes and the length of the chord of said vanes;

a second side of the mask has a dimension between the fifth part of the chord of said vanes and the height of the blade of said vanes.

These dimensions are empirically determined as a function of the considered zone of the casing and from the fragmentary diagram of the vanes which determines the shape and dimensions of the impact zones of fragments. The fragmentary diagram of the vanes is unique to each vane technology (shrouded-tip vane, fence vanes, wide chord vanes . . . ).

Each mask is associated with a specific chart used for determining a level of harmfulness from depth and length information of each impact to be considered.

The step of delimiting an inspection area containing the first impact is made by means of tracers and an associated calculator.

Each chart relates a measured value of the depth of the impact to be considered and a range of values comprising a measured value of the length of the impact to be considered to a level of harmfulness.

The range of values comprising the measured value of the length of the impact to be considered has an amplitude of at least 5 millimeters for impacts having a length lower than 30 millimeters.

The method includes the further step of, prior to the measuring step, excluding from the set of impacts to be considered the impacts having a depth lower than 0.1 millimeters.

The invention and its different applications will be better understood upon reading the following description and upon examining the accompanying figures.

BRIEF DESCRIPTION OF THE FIGURES

The figures are only shown by way of indicative and in no way restricting purposes of the invention. The figures show.

DETAILED DESCRIPTION OF AT LEAST ONE EMBODIMENT OF THE INVENTION

Unless otherwise set out, a same element appearing in different figures has a single reference.

Figure 1:
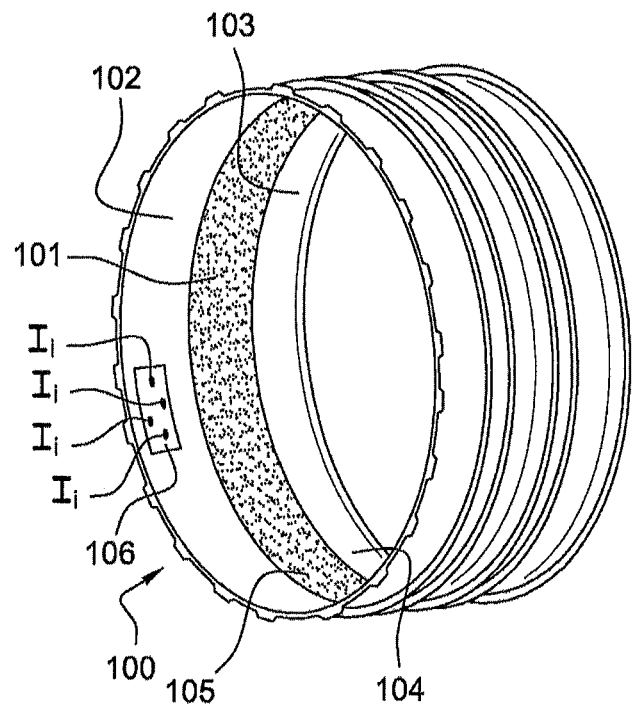
in FIG. 1, a schematic representation of an exemplary fan casing on which the method according to the invention can be implemented.

In FIG. 1, the fan casing 100 has been represented, which is typically of aluminium. A plurality of vanes, not shown, are usually provided by forming a disk inside the casing 100.

The casing 100 has an internal face 104, a central part 101 of which has an abradable zone 105. In practice, the abradable zone 105 is provided facing the vanes; its function is to restrict the deterioration in the casing when the vanes slightly rub on the internal face 104.

On either side of the abradable zone, there are respectively an upstream zone 101, which is the first zone met by air entering the casing 100, and a downstream zone 103, which is the zone through which air passes once the same has been accelerated by the moving vanes.

Figure 2:
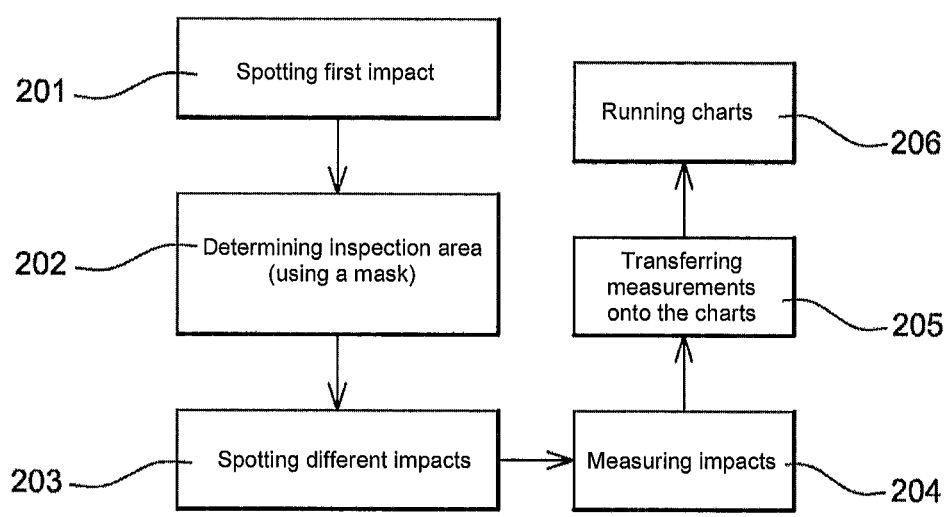
in FIG. 2, a diagram illustrating an exemplary implementation of the method according to the invention.

FIG. 2 is a diagram illustrating an exemplary implementation of the method according to the invention.

In this figure, the successive steps to be performed have been represented for the exemplary implementation considered of the method according to the invention. There are to be distinguished, successively:

A first step 201, called a step of spotting a first impact I1 (visible in FIG. 1) on the internal face 104 of the casing. This spotting is advantageously visually performed by a controller. In an improved mode of the method according to the invention, tracer type sensors can be used to spot the first impact; but the visual solution, because of its simple implementation, is advantageous. Advantageously, the first impact is only maintained if it has a depth higher than 0.1 millimeters;

a second step 202, called a step of determining an inspection area 106 (visible in FIG. 1), wherein a closed area of the internal face 104 is determined, closed area in which is the first impact, and on which the controller will measure a total level of harmfulness. The level of harmfulness is the value which will allow to determine if the set of impacts detected in the sensitive zone is considered as having too much deteriorated the casing considered for the same to be able to be still in operation, that is its specific retention, at the inspection area, has not reduced the specific retention of the casing 100 prohibitively.

The closed area selected is substantially determined as a function of vane fragments likely to impact the internal face 104 of the casing 100 when the same are broken off.

A tool is used to delimit the inspection area. Advantageously, in the invention, use of a mask to delimit the inspection area is provided; a mask being merely a material element, for example of cardboard, or of plastics, wherein an aperture which makes up the shape and dimensions of the mask, and consequently the shape and dimensions of the inspection area has been provided. In more elaborate but less readily implemented exemplary implementations, the inspection area is delimited by using a calculator which manages the displacement of tracers in the inspection area stored by the calculator.

Under a vane loss, that is when a vane is detached, the casing is differently biased depending on the zones been studied. Indeed, during a vane loss, the blade is fragmented into several pieces having different sizes and masses which will then impact the casing with variable speeds depending on the zone (upstream zone, downstream zone, abradable zone). Thus, the inspection area has advantageously a shape and/or dimensions which are variable depending on the zone considered.

In advantageous implementations of the invention on a CFM56-7B engine, a mask having a rectangular opening whose dimensions are 20 millimeters width and 71 millimeters length is selected for the upstream zone, and a square shaped mask having a side 250 millimeters for the downstream zone.

The controller searches for a critical area thanks to the mask. This critical area corresponds to that including a maximum of harmful impacts that can penetrate the window. By a harmful impact, it is meant typically the impacts the depth of which is higher than 0.1 millimeters. The inspector will thus have to repeat the inspection operations for all the possible impact combinations.

A third step 203 during which the controller spots different impacts Ii (visible in FIG. 1) present in the inspection area 106.

Figure 3:
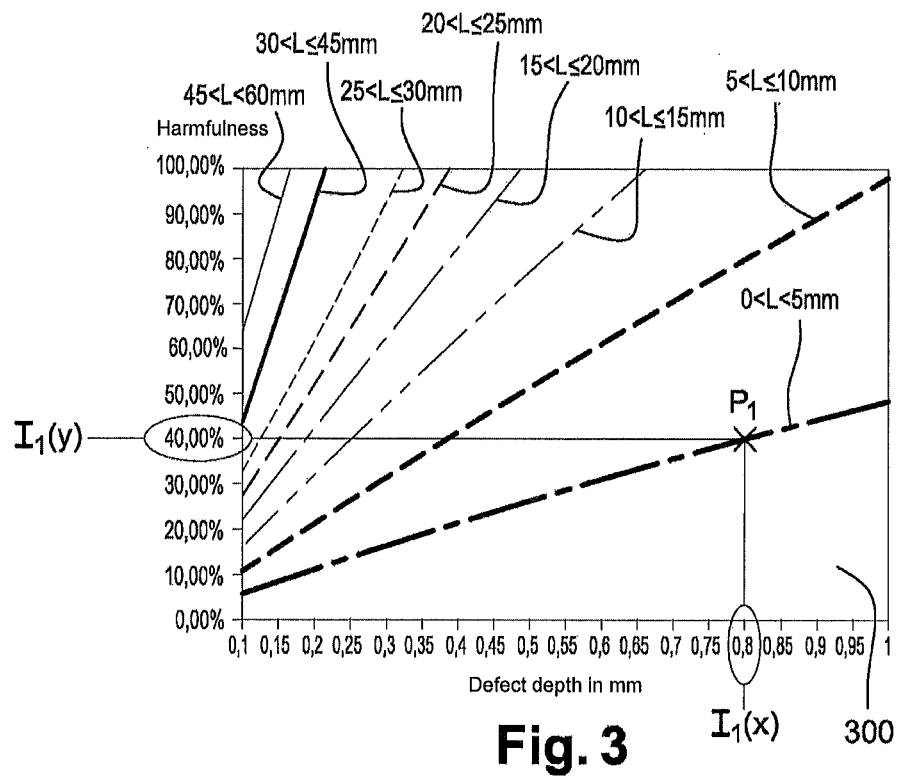
in FIG. 3, a first exemplary chart likely to be used in an exemplary implementation of the method according to the invention.
Figure 4:
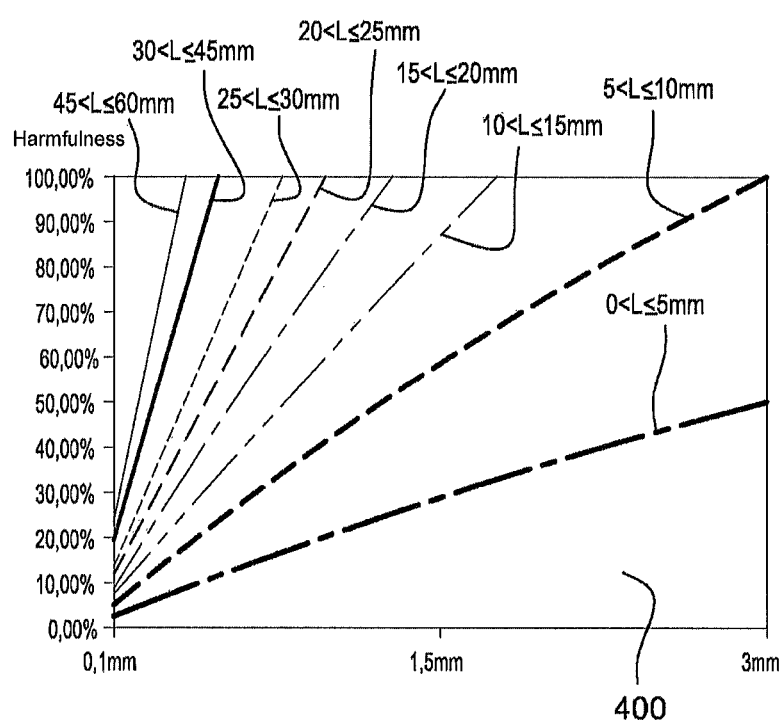
in FIG. 4, a second exemplary chart likely to be used in an exemplary implementation of the method according to the invention.

A fourth step 204 during which the controller measures the depth and length of each impact, advantageously of each harmful impact, of the inspection area delimited by the mask.

a fifth step 205 wherein the controller spots the measurement information on a suitable chart. Advantageously, in the invention, a chart is provided per casing zone (upstream zone, downstream zone, abradable zone). FIG. 3 shows an exemplary advantageous chart 300 used for controls in the upstream zone of the fan casing 100, with functional values, and FIG. 4 shows an exemplary advantageous chart 400 used for controls in the downstream zone of the fan casing 100, with functional values. Thus, advantageously, in the inspection method according to the invention, a mask and a chart are bijectively associated to make the controls.

The charts provided according to the invention are organized the following way:

in abscissa, there are the measured values of the impact depths;

in ordinate, there is a percentage of harmfulness of each impact considered in the inspection area;

different curves, line portions in the represented examples, ensure relating an impact depth to a percentage of harmfulness associated with this impact. The curves are made for each length of an observed impact. Advantageously, in order to limit the number of curves, each curve of the chart is representative of a range of values of length of a measured impact.

These charts are designed from a representative population, typically ninety percent of the defects noticed, retained in a statistical distribution of the defects as a function of their lengths. It is attempted to cover a maximum of (depth; length) couples of this representative population using a minimum number of curves. These curves are then optimized by taking into account the inspector feedback and phenomena such as erosion.

A sixth step 206 wherein the controller runs the charts to determine a total harmfulness value for the inspection area to be considered.

Use of the charts by a controller is the following: once he/she has determined the inspection area, he/she refers, for the first impact I1 of the inspection area, to the abscissa axis at which he/she transfers the value I1 (X) of the measured depth, 0.8 millimeters in the example illustrated in FIG. 3. He/she then searches from the chart curves, which curve corresponds to the measured length for the impact considered. In the example represented, it is considered that the length of the first impact I1 is 3 millimeters. He/she then projects the abscissa I1 (X) onto the curve considered to obtain a point P1 of the chart. By reading, on the ordinate axis, the value of the ordinate I1 (Y) of the point P1, the level of harmfulness value is thus obtained for the first point considered. In the example represented, this value is 40 percent. The operation is repeated for all the impact points spotted in the inspection area during step 203. By summing the different level of harmfulness values obtained for each of the impact points to be considered, the total harmfulness value is obtained for the inspection area considered. If this value is higher than one hundred percent, it is considered that the casing 100 cannot be used as such.

It will be noted that the charts of FIGS. 3 and 4 have been reduced to only take into account impacts having a depth higher than 0.1 mm. By only considering these impacts, a significant decrease in the inspection time is achieved.

The inspection method according to the invention makes the following main advantages clearer:

High number of defects covered:

The number of defects covered by this inspection is dramatically increased relative to the use of current criteria.

Decrease in the inspection time:

Instead of recording three parameters per impact (length, depth and inter-defect distance), the controller now only records two of them; the third parameter being replaced by the use of a mask or an equivalent means. Furthermore, taking into account only impact depths higher than 0.1 mm decreases the number of impacts controlled at least by two with respect to the methods used in the state of the art.

Flexibility of the means and simple implementation:

The simplicity and low overall space of the mask-chart tools make it possible to run them in any maintenance facilities and also allow for inspections under wings, which is a significant advantage.

In a particular embodiment of the invention, use of automatic control means using a "tracer type" measured means coupled to a software for calculating the defect harmfulness (programmed using charts) is provided. If this embodiment is more expensive and takes more overall space than the implementation using masks, a possible implementation of the method according to the invention remains.

The invention claimed is:

1. A method for inspecting impacts present on an internal face of a fan casing, said method comprising:
   spotting a first impact present in the internal face of the fan casing;
   delimiting an inspection area including said first impact;
   spotting different impacts present on the delimited inspection area, said different spotted impacts forming a set of impacts to be considered;
   measuring, for each impact to be considered, the depth and length of said impact;
   for each impact to be considered, determining a level of harmfulness value, using at least one chart relating the depth and length of each impact to be considered to a level of harmfulness, wherein for the depth of the impact, the chart provides different levels of harmfulness that depend on the length of the impact;
   determining, for the inspection area including the first impact, a total level of harmfulness value by adding the level of harmfulness determined for each impact to be considered.

2. The method according to claim 1, wherein delimiting the inspection area containing the first impact is performed by a mask.

3. The method according to claim 2, wherein the mask is rectangular in shape and has the following characteristics:
   a first side of the mask has a dimension between a fifth part of a chord of casing vanes and the length of the chord of said vanes;
   a second side of the mask has a dimension between the fifth part of the chord of said vanes and the height of a blade of said vanes.

4. The method according to claim 2, wherein the dimensions of the mask depend on the location of the inspection area, a first mask having first dimensions being used for an upstream zone of the casing and/or a second mask having second dimensions being used for an abradable zone of the casing and/or a third mask having third dimensions being used for a downstream zone of the casing.

5. The method according to claim 4, wherein the first mask is rectangular in shape, having a length 71 millimeters within ten percent, and a width 20 millimeters within ten percent, and/or the third mask is square in shape, having a side 250 millimeters within ten percent.

6. The method according to claim 5, wherein each mask is associated with a specific chart used for determining a level of harmfulness from depth and length information of each impact to be considered.

7. The method according to claim 1, wherein delimiting the inspection area containing the first impact is performed by tracers and an associated calculator.

8. The method according to claim 1, wherein each chart relates a measured value of the depth of the impact to be considered and a range of values comprising a measured value of the length of the impact to be considered to a level of harmfulness.

9. The method according to claim 8, wherein the range of values comprising the measured value of the length of the impact to be considered has an amplitude of at least 5 millimeters for impacts having a length lower than 30 millimeters.

10. The method according to claim 1, comprising, prior to the measuring, excluding from the set of impacts to be considered the impacts having a depth lower than 0.1 millimeters.

11. The method according to claim 1, wherein the chart correlates the level of harmfulness to the depth of the impact for different ranges of lengths of impacts.

* * * * *